United States Patent [19] [11] 4,364,385
Lossef [45] Dec. 21, 1982

[54] INSULIN DELIVERY DEVICE

[76] Inventor: Steven V. Lossef, 125-15 Cronston Ave., Belle Harbor, N.Y. 11694

[21] Appl. No.: 243,494

[22] Filed: Mar. 13, 1981

[51] Int. Cl.³ ............................................. A61J 7/00
[52] U.S. Cl. ................................. 128/213 R; 128/260
[58] Field of Search .................... 424/19, 20; 128/213, 128/260, 1 R, 635

[56] References Cited

U.S. PATENT DOCUMENTS

| | | | |
|---|---|---|---|
| 4,036,227 | 7/1977 | Zaffaroni et al. | 128/260 |
| 4,077,407 | 3/1978 | Theeuwes et al. | 128/260 |
| 4,140,121 | 2/1979 | Kühl et al. | 128/213 R |
| 4,140,122 | 2/1979 | Kühl et al. | 128/260 |
| 4,217,894 | 8/1980 | Franetzki | 128/213 R |
| 4,240,438 | 12/1980 | Updike et al. | 128/635 |
| 4,245,634 | 1/1981 | Albisser et al. | 128/260 |

Primary Examiner—Richard J. Apley
Assistant Examiner—T. J. Wallen
Attorney, Agent, or Firm—Mitchell B. Wasson; Martin P. Hoffman

[57] ABSTRACT

An insulin delivery device comprised of a compartment limited by a semipermeable, ionically charged membrane, containing the enzymes glucose oxidase and catalase, is disclosed. The enclosed enzymes provide a means for varying the permeabiity of the membrane to stored insulin deposited within the compartment according to the magnitude of glucose concentration outside the compartment, thus facilitating continuous, physiologically regulated delivery of insulin to tissues. This device may be applicable for intracorporeal or extracorporeal use.

6 Claims, 1 Drawing Figure

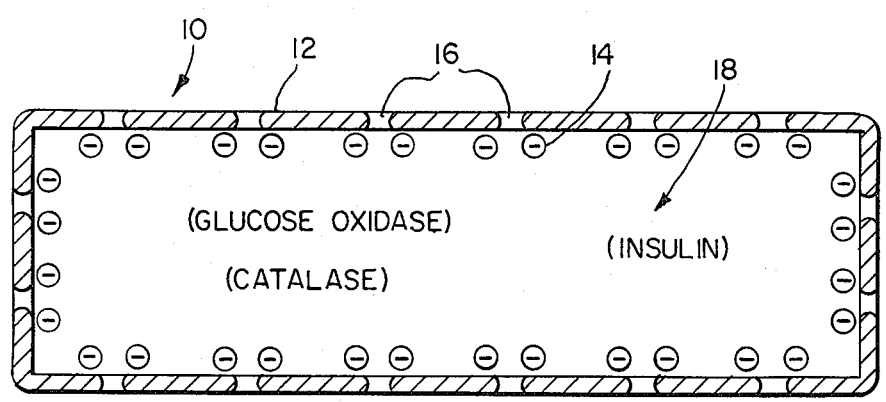

INSULIN DELIVERY DEVICE

BACKGROUND OF THE INVENTION

This invention relates to an insulin delivery device which permits regulation of the permeability of a negatively charged, porous membrane to stored insulin, according to the concentration of glucose in circulating body fluids. More specifically, the glucose is oxidized by the enzyme glucose oxidase to gluconic acid, which causes an alteration in the net ionic charge of the membrane, hence varying the permeability of insulin through the membrane pores. In this manner, continuous insulin release may be modified instantaneously in order to deliver appropriate doses to diabetics. The device may be used either intracorporeally or extracorporeally.

Diabetes mellitus is a disease characterized by the absence of or inappropriate secretion of insulin by the pancreas, resulting in high concentrations of glucose circulating in the blood. Periodic injection of slowly released insulin is a common treatment for this disorder, and results in a salutory decrease in the blood glucose levels. However, since the tissue demands for insulin change continuously throughout the day, such periodic administration of insulin is unable to precisely and instantaneously maintain normal glucose blood levels. In fact, administration of insulin at a continuous, uniform rate of release often has limited effect in preventing the long-term complications of diabetic hyperglycemia, namely vascular degeneration. This could lead to premature retinopathy, glomerulosclerosis, atherosclerosis, neuropathy, trophic ulceration cataract formation, glycosylation of proteins, complications of pregnancy, etc. Furthermore, simple administration of insulin is often suboptimal therapy for control of hyperglycemia in "brittle diabetics". Hence, many attempts have been made to produce devices for continuously providing appropriate amounts of insulin.

DESCRIPTION OF THE PRIOR ART

Several drug delivery devices using simple, porous, membrane-limited drug reservoirs have been described (U.S. Pat. Nos. 3,926,188; 3,993,072; 3,765,414). In these devices, continuous rates of drug delivery are possible using implantable, membrane-limited drug-reservoir compartments. However, these devices are unable to continuously vary the permeabilty of the membrane according to physiological requirement for the drug, and hence are unable to vary the rate of drug delivery.

Another approach to drug delivery is described in two patents involving an electro-osmotic pump which propels a drug solution, providing continuous, controllable release of medication. U.S. Pat. No. 4,140,121 describes an implantable pump in which liquid is transported through an ion exchange diaphragm by electro-osmosis due to an electric field between two hydrogen electrodes connected to each other by way of a hydrogen line, with compensation for hydrogen loss by means of stored compressed hydrogen, an auxiliary glucose or consumable metal electrode, or a transition metal compound storing hydrogen, whereby the pumped liquid produces pressure in a liquid chamber tensionally connected to a variable volume medicine reservoir, resulting in extrusion and delivery of drug solution to the tissues. U.S. Pat. No. 4,140,122 describes a similar implantable pump device consisting of a propellant chamber (utilizing a volatile liquid or hydrolytically produced gas as a propellant), tensionally connected via an elastic partition to a variable volume medicine reservoir, with an electro-osmotic regulating valve comprising an ion exchange diaphragm arranged between two porous silver/silver chloride electrodes. Both of these devices provide controllable but uniform rates of drug delivery, but without any provision for instantaneously coupling pump flow rate with physiological requirement for drug delivery to tissues.

In an effort to infuse insulin depending upon instantaneous blood glucose concentrations, a device described in U.S. Pat. No. 4,055,175 is designed to determine serial blood glucose concentrations via a glucose electrode which converts this to an electric current signal, which is subsequently processed by a computer, which ultimately controls the rate of an insulin infusion pump. Detailed plans for the glucose sensor component of such a computer-controlled device are disclosed in U.S. Pat. No. 3,539,455, in which an electrode measures the amount of hydrogen peroxide generated by the oxidation of glucose, which is catalyzed by the enzyme glucose oxidase, which is contained within a porous, semipermeable, membrane-limited electrode chamber.

These computerized devices have the great advantage of providing accurate and physiologically appropriate amounts of insulin to tissues, thus, continuously maintaining normal glucose blood concentrations. However, they have the disadvantages of bulkiness (due to the size of the computer, pump and sensor), continuous electrical power requirements, possible breakdown of moving parts, and high cost.

In an effort to precisely regulate insulin release according to blood glucose concentrations, recent attempts have been made to (intravenously or intraperitoneally) implant animal-derived, insulin-producing, viable pancreatic islet cells (which would synthesize and release insulin at rates determined by levels of blood glucose), contained in semipermeable membrane-limited chambers. These semipermeable membrane-limited chambers permit diffusion of glucose and nutrients for the cells into the chamber, permit diffusion of insulin and cellular wastes out of the chamber and into tissues, and prevent immunological rejection of the heteroantigenic islet cells.

Although these encapsulated pancreatic islet cell devices promise to deliver physiologically appropriate amounts of insulin determined by concentrations of glucose in the blood, major disadvantages include difficulty in obtaining sufficient amounts of viable islet cells for the vast number of diabetics in this country, and difficulty in keeping these delicate cells alive and functioning properly.

Accordingly, the object of the present invention is to provide a novel insulin delivery device which delivers physiologically appropriate amounts of insulin to tissues, determined by glucose concentrations in the blood, thus overcoming the aforesaid disadvantages associated with the prior art devices.

For a better understanding of the invention, together with other and further objects, reference is made to the following description, taken in conjunction with the accompanying drawing; and its scope will be pointed out in the appended claims.

BRIEF DESCRIPTION OF THE DRAWING

The FIGURE shows a schematic drawing of the insulin secreting component.

DETAILED DESCRIPTION OF THE INVENTION

The present invention is directed to a semipermeable, membrane-limited compartment 10 containing insulin (including, but not limited to crystalline and other slowly dissolving forms) and the enzymes glucose oxidase (EC 1.1.3.4.) and catalase (EC 1.11.1.6.), both of which may be used in the soluble and/or immobilized forms. The semipermeable membrane 12 of this compartment has pores of definite size (approximately 6500 dalton cut-off size), and has a net negative surface charge 14. This membrane allows glucose (with a molecular weight of 180 daltons, much smaller than the membrane pore size cut-off of 6500 daltons) to freely diffuse into the compartment; hence, the concentration of glucose inside the compartment is related to that outside.

Once within the compartment, the enzymes contained therein convert the glucose into gluconic acid by a series of enzymatic steps to be outlined below. The gluconic acid thus formed (with a dissociation constant (Keq) equal to $2.5 \times 10^{-4}$) dissociates to release hydrogen ions ($H^{\oplus}$). Insulin (with Pisolectric=5.33) having a net negative charge at physiological pH of 7.4, and the moderate net negative surface charge of the semipermeable membrane, and the 6500 dalton pore size of the semipermeable membrane (which is only slightly larger than that of insulin, which has a molecular weight of approximately 6000 daltons) normally tend to impede the diffusional egress of insulin from depot stores within the compartment into the body tissues. The important and novel point of this device is that as more hydrogen ions ($H^{\oplus}$) are formed in response to higher glucose concentrations, the net negative charge of the insulin and the semipermeable membrane is reduced, thus reducing the electrostatic charge repulsion between the insulin and the membrane surrounding the pores, resulting in an increase in the rate of diffusional egress of insulin through the membrane pores. This is an ideal situation since diabetics require the greatest amount of insulin to be released at the times when their blood glucose concentrations are high. As the blood concentration of glucose decreases, less hydrogen ions ($H^{\oplus}$) are enzymatically formed within the compartment from the substrate glucose, with a subsequent increase in negative ionic charges and electrostatic repulsion between the membrane and the insulin, thus impeding diffusional egress of insulin through the membrane pores. The use of slowly dissolving or crystalline insulin may help to dampen changes in the rate of insulin diffusional release.

The enzymatic reactions which occur within the compartment are as follows:

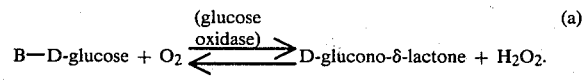

(a)

(b)

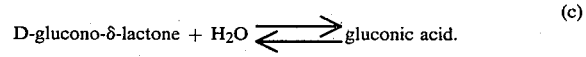

(c)

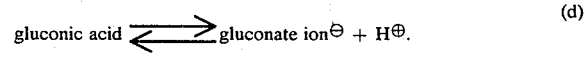

(d)

The glucose oxidase contained within the compartment produces the gluconic acid from the substrate glucose. The catalase contained within the compartment functions to rapidly degrade the hydrogen peroxide formed during the oxidation of glucose, before it can exert any oxidative action on the stored insulin or enzymes. The enzymes have much larger sizes than that of the membrane pores, preventing their leakage from the compartment. Immobilization of the enzymes (using matrices such as agarose, cellulose, or polyacrylamide, etc.) may significantly increase stability and activity. Ratios of insulin, enzymes, net membrane charge, membrane pore size, and surface area of the compartment may all be varied to achieve optimal characteristics regarding response of insulin release to glucose concentrations.

Possible materials which may be employed as the semipermeable membrane for use in this device include but are not limited to cellulose polymers, polycarbamate, nitrocellulose, and other polymers.

This device may be used for extracorporeal and/or intracorporeal use, with possible implantation in a variety of sites, including intraperitoneal, intramuscular, subcutaneous, and intravenous sites, or possible extracorporeal use by bathing with blood from a continuous or intermittent flow, indwelling intravenous catheter, or other means of exposure of the device to body fluids.

Although the present invention utilizes the enzymes glucose oxidase and catalase to react with the glucose to form hydrogen ions, it is noted that other enzymes which liberate the hydrogen ion from the glucose would operated with equal efficaciousness.

While there have been described what are believed to be the preferred embodiments of the present invention, those skilled in the art will recognize that various changes and modifications may be made thereto without departing from the spirit of the invention, and it is intended to claim all such embodiments as fall within the true scope of the invention.

What is claimed is:

1. An insulin delivery device comprising:
   a compartment containing insulin therein, said compartment limited by a semipermeable membrane having a plurality of pores permeable to glucose and exhibiting a net negative surface charge, said compartment adapted to contact circulating body fluids including glucose; and
   enzymes contained in said compartment capable of liberating hydrogen ions from glucose diffused through said pores, from said body fluids, the molecular size of said enzymes being greater than the size of the pores of said compartment and the molecular size of the insulin being slightly smaller than the size of the pores of said compartment;
   whereby, as the concentration of positive hydrogen ions increases with an increase of glucose concentration, the net negative charge of the semipermeable membrane is reduced providing an increase in the rate of diffusion of the insulin through the pores as a function of the increase of glucose concentration in the circulating body fluids.

2. An insulin delivery device in accordance with claim 1 wherein said enzymes are glucose oxidase and catalase.

3. An insulin delivery device in accordance with claims 1 and 2 whereby the pore size of said semipermeable membrane is approximately 6500 daltons.

4. An insulin delivery device in accordance with claim 2 wherein said glucose oxidase and said catalase convert the glucose into gluconic acid which dissociates into negative gluconate ions and positive hydrogen ions.

5. A method for providing a controlled release of insulin comprising the steps of:

providing a compartment limited by a semipermeable membrane having a negative surface charge and containing enzymes and insulin therein, said semipermeable membrane having pores which are smaller that the molecular size of the enzymes and are slightly larger than the molecular size of the insulin;

placing said compartment in contact with circulating body fluid containing a varying concentration of glucose, said glucose capable of diffusing through the pores of said semipermeable membrane; and reacting the glucose with said enzymes to liberate positive hydrogen ions, the concentration of said hydrogen ions being a function of the concentration of the glucose;

whereby as the concentration of positive hydrogen ions increases with an increase of glucose concentration, the net negative charge of the semipermeable membrane is reduced providing an increase in the rate of diffusion of the insulin through the pores as a function of the glucose concentration in the circulating body fluids.

6. A method for providing a controlled release of insulin in accordance with claim 5 wherein said enzymes are glucose oxidase and catalase.

* * * * *